(12) United States Patent
Vidlund et al.

(10) Patent No.: US 10,952,844 B2
(45) Date of Patent: *Mar. 23, 2021

(54) TETHERS FOR PROSTHETIC MITRAL VALVE

(71) Applicant: Tendyne Holdings, Inc., St. Paul, MN (US)

(72) Inventors: Robert M. Vidlund, Forest Lake, MN (US); Kemal Schankereli, Stillwater, MI (US)

(73) Assignee: Tendyne Holdings, Inc., St. Paul, MN (US)

( * ) Notice: Subject to any disclaimer, the term of this patent is extended or adjusted under 35 U.S.C. 154(b) by 515 days.

This patent is subject to a terminal disclaimer.

(21) Appl. No.: 15/819,419

(22) Filed: Nov. 21, 2017

(65) Prior Publication Data

US 2018/0078368 A1    Mar. 22, 2018

Related U.S. Application Data

(63) Continuation of application No. 13/715,234, filed on Dec. 14, 2012, now Pat. No. 9,827,092.

(Continued)

(51) Int. Cl.
*A61F 2/24* (2006.01)
*A61B 17/04* (2006.01)

(52) U.S. Cl.
CPC ........ *A61F 2/2418* (2013.01); *A61B 17/0401* (2013.01); *A61F 2/2439* (2013.01);
(Continued)

(58) Field of Classification Search
CPC ........ A61F 2/24; A61F 2/2409; A61F 2/2427; A61F 2/2439; A61F 2/2442;
(Continued)

(56) References Cited

U.S. PATENT DOCUMENTS

| 2,697,008 A | 12/1954 | Rowley |
| 3,409,013 A | 11/1968 | Berry |

(Continued)

FOREIGN PATENT DOCUMENTS

| CN | 1486161 | 3/2004 |
| CN | 1961845 A | 5/2007 |

(Continued)

OTHER PUBLICATIONS

US 9,155,620 B2, 10/2015, Gross et al. (withdrawn)

(Continued)

*Primary Examiner* — Tan-Uyen T Ho
*Assistant Examiner* — Chima U Igboko
(74) *Attorney, Agent, or Firm* — Lerner, David, Littenberg, Krumholz & Mentlik, LLP

(57) ABSTRACT

This invention relates to the design and function of a single-tether compressible valve replacement prosthesis which can be deployed into a beating heart without extracorporeal circulation using a transcatheter delivery system. The design as discussed combats the process of wear on anchoring tethers over time by using a plurality of stent-attached, centering tethers, which are themselves attached to a single anchoring tether, which extends through the ventricle and is anchored to a securing device located on the epicardium.

17 Claims, 11 Drawing Sheets

Related U.S. Application Data

(60) Provisional application No. 61/576,366, filed on Dec. 16, 2011.

(52) U.S. Cl.
CPC . *A61B 2017/0403* (2013.01); *A61B 2017/048* (2013.01); *A61B 2017/0417* (2013.01); *A61F 2/2457* (2013.01); *A61F 2/2487* (2013.01); *A61F 2220/0008* (2013.01); *A61F 2220/0016* (2013.01); *A61F 2230/0078* (2013.01)

(58) Field of Classification Search
CPC .... A61F 2/2445; A61F 2/2451; A61F 2/2418; A61F 2/2457; A61F 2/2487; A61F 2002/249; A61F 2220/0008; A61F 2220/0016; A61F 2220/0025; A61F 2220/0033; A61F 2220/0041; A61F 2220/0075; A61F 2220/0091; A61F 2220/0083; A61B 17/0401; A61B 2017/0403; A61B 2017/048; A61B 2017/04; A61B 2017/0406; A61B 2017/0408; A61B 2017/0417
See application file for complete search history.

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Sammuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane et al. |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |

(56) References Cited

U.S. PATENT DOCUMENTS

| | | |
|---|---|---|
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro et al. |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasakaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely et al. |
| 6,575,252 B2 | 6/2003 | Reed |
| 6,582,462 B1 | 6/2003 | Andersen et al. |
| 6,605,112 B1 | 8/2003 | Moll |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin et al. |
| 6,976,543 B1 | 12/2005 | Fischer |
| 6,997,950 B2 | 2/2006 | Chawia |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 * | 1/2008 | Bloom .................. A61F 2/2487 606/151 |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |

(56) References Cited

U.S. PATENT DOCUMENTS

| | | |
|---|---|---|
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Thambar et al. |
| 8,986,376 B2 | 3/2015 | Solem |
| 9,011,522 B2 | 4/2015 | Annest et al. |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Sequin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,895,221 B2 | 2/2018 | Vidlund |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183787 A1* | 12/2002 | Wahr ............... A61B 17/0057 606/213 |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | Van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |

(56) References Cited

U.S. PATENT DOCUMENTS

| | | |
|---|---|---|
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariiler |
| 2007/0270932 A1 | 11/2007 | Headley et al. |
| 2007/0270943 A1 | 11/2007 | Solem |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1* | 4/2008 | Machold ............ A61B 17/0057 623/2.1 |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1* | 11/2009 | Rowe ................ A61B 17/0401 623/2.18 |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |

(56) References Cited

U.S. PATENT DOCUMENTS

| | | |
|---|---|---|
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0077667 A1* | 3/2011 | Singhatat ........... A61B 17/0401 606/139 |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1* | 12/2011 | Schankereli .......... A61F 2/2436 623/2.11 |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0165930 A1 | 6/2012 | Gifford et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund et al. |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James et al. |
| 2015/0202044 A1 | 7/2015 | Chau et al. |
| 2015/0216653 A1 | 8/2015 | Freudenthanl |
| 2015/0216660 A1 | 8/2015 | Pintor et al. |
| 2015/0223820 A1 | 8/2015 | Olson et al. |
| 2015/0223934 A1 | 8/2015 | Vidlund et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean et al. |
| 2015/0335424 A1 | 11/2015 | McLean et al. |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |
| 2016/0074160 A1 | 3/2016 | Christianson et al. |

(56) References Cited

U.S. PATENT DOCUMENTS

| | | | |
|---|---|---|---|
| 2016/0106537 A1 | 4/2016 | Christianson et al. |
| 2016/0113764 A1 | 4/2016 | Sheahan et al. |
| 2016/0143736 A1 | 5/2016 | Vidlund et al. |
| 2016/0151155 A1 | 6/2016 | Lutter et al. |
| 2016/0206280 A1 | 7/2016 | Vidlund et al. |
| 2016/0242902 A1 | 8/2016 | Morriss et al. |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau et al. |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2018/0028314 A1 | 2/2018 | Ekvall et al. |
| 2018/0078370 A1 | 3/2018 | Kovalsky et al. |

FOREIGN PATENT DOCUMENTS

| | | |
|---|---|---|
| CN | 2902226 | 5/2007 |
| CN | 101146484 | 3/2008 |
| CN | 101180010 | 5/2008 |
| CN | 101984938 | 3/2011 |
| CN | 102869317 | 1/2013 |
| CN | 102869318 | 1/2013 |
| CN | 102869321 | 1/2013 |
| CN | 103220993 | 7/2013 |
| CN | 102639179 B | 10/2014 |
| DE | 2246526 | 3/1973 |
| DE | 19532846 | 3/1997 |
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049815 | 4/2002 |
| DE | 102006052564 | 12/2007 |
| DE | 102006052710 | 5/2008 |
| DE | 102007043830 A1 | 4/2009 |
| DE | 102007043831 | 4/2009 |
| EP | 0103546 | 5/1988 |
| EP | 1057460 | 12/2000 |
| EP | 1088529 | 4/2001 |
| EP | 1469797 | 11/2005 |
| EP | 2111800 | 10/2009 |
| EP | 2193762 | 6/2010 |
| EP | 2747707 | 4/2015 |
| EP | 2918248 | 9/2015 |
| EP | 2278944 | 3/2016 |
| FR | 2788217 | 7/2000 |
| FR | 2815844 | 5/2002 |
| JP | 2003-505146 | 2/2003 |
| JP | 2005-515836 | 6/2005 |
| JP | 2009-514628 | 4/2009 |
| JP | 2013-512765 | 4/2013 |
| NL | 1017275 | 8/2002 |
| SU | 1271508 | 11/1986 |
| WO | WO 92/17118 | 10/1992 |
| WO | WO 93/01768 | 2/1993 |
| WO | WO 98/29057 | 7/1998 |
| WO | WO 99/40964 | 8/1999 |
| WO | WO 99/47075 | 9/1999 |
| WO | WO 2000/018333 | 4/2000 |
| WO | WO 2000/030550 | 6/2000 |
| WO | WO 2000/041652 | 7/2000 |
| WO | WO 2000/047139 | 8/2000 |
| WO | WO 2001/035878 | 5/2001 |
| WO | WO 2001/049213 | 7/2001 |
| WO | WO 2001/054624 | 8/2001 |
| WO | WO 2001/054625 | 8/2001 |
| WO | WO 2001/056512 | 8/2001 |
| WO | WO 2001/061289 | 8/2001 |
| WO | WO 2001/076510 | 10/2001 |
| WO | WO 2001/082840 | 11/2001 |
| WO | WO 2002/004757 | 1/2002 |
| WO | WO 2002/022054 | 3/2002 |
| WO | WO 2002/028321 | 4/2002 |
| WO | WO 2002/036048 | 5/2002 |
| WO | WO 2002/041789 | 5/2002 |
| WO | WO 2002/043620 | 6/2002 |
| WO | WO 2002/049540 | 6/2002 |
| WO | WO 2002/076348 | 10/2002 |
| WO | WO 2003/003943 | 1/2003 |
| WO | WO 2003/030776 | 4/2003 |
| WO | WO 2003/047468 | 6/2003 |
| WO | WO 2003/049619 | 6/2003 |
| WO | WO 2004/019825 | 3/2004 |
| WO | WO 2005/102181 | 11/2005 |
| WO | WO 2006/014233 | 2/2006 |
| WO | WO 2006/034008 | 3/2006 |
| WO | WO 2006/064490 | 6/2006 |
| WO | WO 2006/070372 | 7/2006 |
| WO | WO 2006/113906 | 10/2006 |
| WO | WO 2006/127756 | 11/2006 |
| WO | WO 2007/081412 | 7/2007 |
| WO | WO 2008/005405 | 1/2008 |
| WO | WO 2008/035337 | 3/2008 |
| WO | WO 2008/091515 | 7/2008 |
| WO | WO 2008/125906 | 10/2008 |
| WO | WO 2008/147964 | 12/2008 |
| WO | WO 2009/024859 | 2/2009 |
| WO | WO 2009/026563 | 2/2009 |
| WO | WO 2009/045338 | 4/2009 |
| WO | WO 2009/132187 | 10/2009 |
| WO | WO 2010/090878 | 8/2010 |
| WO | WO 2010/098857 | 9/2010 |
| WO | WO 2010/121076 | 10/2010 |
| WO | WO 2011/017440 | 2/2011 |
| WO | WO 2011/022658 | 2/2011 |
| WO | WO 2011/069048 | 6/2011 |
| WO | WO 2011/072084 | 6/2011 |
| WO | WO 2011/106735 | 9/2011 |
| WO | WO 2011/109813 | 9/2011 |
| WO | WO 2011/159342 | 12/2011 |
| WO | WO 2011/163275 | 12/2011 |
| WO | WO 2012/027487 | 3/2012 |
| WO | WO 2012/036742 | 3/2012 |
| WO | WO 2012/095116 | 7/2012 |
| WO | WO 2012/177942 | 12/2012 |
| WO | WO 2013/045262 | 4/2013 |
| WO | WO 2013/059747 | 4/2013 |
| WO | WO 2013/096411 | 6/2013 |
| WO | WO 2013/175468 | 11/2013 |
| WO | WO 2014/121280 | 8/2014 |
| WO | WO 2014/144937 | 9/2014 |
| WO | WO 2014/162306 | 10/2014 |
| WO | WO 2014/189974 | 11/2014 |
| WO | WO 2014/210124 | 12/2014 |
| WO | WO 2015/051430 | 4/2015 |
| WO | WO 2015/058039 | 4/2015 |
| WO | WO 2015/063580 | 5/2015 |
| WO | WO 2015/065646 | 5/2015 |
| WO | WO 2015/120122 | 8/2015 |
| WO | WO 2015/138306 | 9/2015 |
| WO | WO 2015/173609 | 11/2015 |
| WO | WO 2016/112085 | 7/2016 |
| WO | WO 2016/126942 | 8/2016 |
| WO | WO 2016/168609 | 10/2016 |
| WO | WO 2016/196933 | 12/2016 |
| WO | WO 2017/096157 | 6/2017 |
| WO | WO 2017/132008 | 8/2017 |

(56) References Cited

FOREIGN PATENT DOCUMENTS

| WO | WO 2017/218375 | 12/2017 |
|---|---|---|
| WO | WO 2018/005779 | 1/2018 |
| WO | WO 2018/013515 | 1/2018 |

OTHER PUBLICATIONS

Office Action for U.S. Appl. No. 13/715,234, dated Mar. 13, 2015, 17 pages.
Office Action for U.S. Appl. No. 13/715,234, dated Nov. 27, 2015, 21 pages.
Office Action for U.S. Appl. No. 13/715,234, dated Aug. 19, 2016, 19 pages.
Office Action for U.S. Appl. No. 13/715,234, dated Apr. 19, 2017, 18 pages.
Al Zaibag, M. et al., "Percutaneous Balloon Valvotomy in Tricuspid Stenosis," British Heart Journal, Jan. 1987, 57(1):51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
Andersen, H. R. et al., "Transluminal implantation of artificial heart valves. Description of a new expandable aortic valve and initial results with implantation by catheter technique in closed chest pigs," European Heart Journal, 1992, 13(5):704-708.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Ashton, R. C., Jr. et al., "Development of an Intraluminal Device for the Treatment of Aortic Regurgitation: Prototype and in Vitro Testing System," Journal of Thoracic and Cardiovascular Surgery, 1996, 112:979-983.
Benchimol, A. et al., "Simultaneous Left Ventricular Echocardiography and Aortic Blood Velocity During Rapid Right Ventricular Pacing in Man," the American Journal of the Medical Sciences, Jan.-Feb. 1977, 273(1):55-62.
Bernacca, G. M. et al., "Polyurethane heart valves: Fatigue failure, calcification, and polyurethane structure," Journal of Biomedical Materials Research, Mar. 5, 1997, 34(3):371-379.
Boudjemline, Y. et al., "Steps Toward the Percutaneous Replacement of Atrioventricular Valves: An Experimental Study," Journal of the American College of Cardiology, Jul. 2005, 46(2):360-365.
Buckberg, G. et al., "Restoring Papillary Muscle Dimensions During Restoration in Dilated Hearts," Interactive CardioVascular and Thoracic Surgery, 2005, 4:475-477.
Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," the Journal of Heart Valve Disease, Jul. 1999, 8:407-415.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
Gray, H., The Aorta, Anatomy of the Human Body, 1918, Retrieved from the Internet <http://www.bartleby.com/107/142.html> , Dec. 10, 2012, 5 pages.
Gray, H., The Heart, Anatomy of the Human Body, 1918, Retrieved from the Internet <http://education.yahoo.com/reference/gray/subjects/subject/138> , Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
Inoue, K. et al., "Clinical Application of Transvenous Mitral Commissurotomy by a New Balloon Catheter," the Journal of Thoracic and Cardiovascular Surgery, 1984, 87:394-402.
Jin, X. Y. et al., "Aortic Root Geometry and Stentless Porcine Valve Competence," Seminars in Thoracic and Cardiovascular Surgery, Oct. 1999, 11(4):145-150.
Knudsen, L. L. et al., "Catheter-implanted prosthetic heart valves. Transluminal catheter implantation of a new expandable artificial heart valve in the descending thoracic aorta in isolated vessels and closed chest pigs," the International Journal of Artificial Organs, 1993, 16(5):253-262.
Kolata, G., "Device That Opens Clogged Arteries Gets a Failing Grade in a New Study," New York Times [online], <http://www.nytimes.com/1991/01/03/health/device-that-opens-clogged-arteries-gets-a-faili . . . ,>, published Jan. 3, 1991, retrieved from the Internet on Feb. 5, 2016, 3 pages.
Lawrence, D. D., "Percutaneous Endovascular Graft: Experimental Evaluation," Radiology, 1987, 163:357-360.
Lozonschi, L., et al. "Transapical mitral valved stent implantation: A survival series in swine," the Journal of Thoracic and Cardiovascular Surgery, 140(2):422-426 (Aug. 2010) published online Mar. 12, 2010, 1 page.
Lutter, G. et al., "Mitral Valved Stent Implantation," European Journal of Cardio-Thoracic Surgery, 2010, 38:350-355, 2 pages.
Ma, L. et al., "Double-crowned valved stents for off-pump mitral valve replacement," European Journal of Cardio-Thoracic Surgery, Aug. 2005, 28(2):194-198.
Moazami, N. et al., "Transluminal aortic valve placement: A feasibility study with a newly designed collapsible aortic valve," ASAIO Journal, Sep./ Oct. 1996, 42(5):M381-M385.
Orton, C., "Mitralseal: Hybrid Transcatheter Mitral Valve Replacement," Retrieved from the Internet: <http:/www.acvs.org/symposium/proceedings2011/data/papers/102.pdf>, pp. 311-312.
Pavcnik, D. et al. "Development and Initial Experimental Evaluation of a Prosthetic Aortic Valve for Transcatheter Placement," Radiology, 1992; 183:151-154.
Porstmann, W. et al., "Der Verschlug des Ductus Arteriosus Persistens ohne Thorakotomie," Thoraxchirurgie Vaskulare Chirurgie, Band 15, Heft 2, Stuttgart, Apr. 1967, pp. 199-203.
Rashkind, W. J., "Creation of an Atrial Septal Defect Without Thoracotomy," the Journal of the American Medical Association, Jun. 13, 1966, 196(11):173-174.
Rashkind, W. J., "Historical Aspects of Interventional Cardiology: Past, Present, Future," Texas Heart Institute Journal, Dec. 1986, 13(4):363-367.
Reul, H. et al., "The Geometry of the Aortic Root in Health, at Valve Disease and After Valve Replacement," J. Biomechanics, 1990, 23(2):181-191.
Rosch, J. et al., "The Birth, Early Years and Future of Interventional Radiology," J Vasc Interv Radiol., Jul. 2003, 4:841-853.
Ross, D. N., "Aortic Valve Surgery," Guy's Hospital, London, 1968, pp. 192-197.
Rousseau, E. P. M. et al., "A mechanical analysis of the closed Hancock heart valve prosthesis," Journal of Biomechanics, 1988, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, J. B., "Experience with New Retrieval Forceps for Foreign Body Removal in the Vascular, Urinary, and Biliary Systems," Radiology, 1990, 176:535-538.
Serruys, P. W. et al., "Stenting of Coronary Arteries. Are we the Sorcerer's Apprentice?," European Heart Journal , Sep. 1989, 10(9):774-782.
"Shape Memory Alloys," Retrieved from the Internet: <http://webdocs.cs.ualberta.ca/~database/MEMS/sma.html>, Feb. 5, 2016, 3 pages.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.

(56) References Cited

OTHER PUBLICATIONS

Synonym for Twist; http://www.thesaurus.com/browse/twist?s=t; as accessed Nov. 10, 2015.
Tofeig, M. et al., "Transcatheter Closure of a Mid-Muscular Ventricular Septal Defect with an Amplatzer VSD Occluder Device," Heart, 1999, 81:438-440.
Uchida, B. T. et al., "Modifications of Gianturco Expandable Wire Stents," Am. J. Roentgenol., May 1988, 150(5):1185-1187.
Watt, A. H. et al., "Intravenous Adenosine in the Treatment of the Supraventricular Tachycardia; a Dose-Ranging Study and Interaction with Dipyridamole," British Journal of Clinical Pharmacology, 1986, 21:227-230.
Webb, J. G. et al., "Percutaneous Aortic Valve Implantation Retrograde from the Femoral Artery," Circulation, 2006, 113:842-850.
Wheatley, D. J., "Valve Prostheses," Rob & Smith's Operative Surgery, Fourth Edition, 1986, pp. 415-424, Butterworths.
Yoganathan, A. P. et al., "The Current Status of Prosthetic Heart Valves," in Polymetric Materials and Artificial Organs, American Chemical Society, 1984, pp. 111-150.

\* cited by examiner

TETHERS FOR PROSTHETIC MITRAL VALVE

CROSS REFERENCE TO RELATED APPLICATIONS

This application is a continuation of U.S. patent application Ser. No. 13/715,234, filed Dec. 14, 2012, which claims priority to U.S. provisional application Ser. No. 61/576,366, filed Dec. 16, 2011, each of the disclosures of which is incorporated by reference herein in its entirety.

FIELD OF THE INVENTION

This invention relates to improved tethering for a transcatheter mitral valve replacement.

BACKGROUND OF THE INVENTION

Valvular heart disease and specifically aortic and mitral valve disease is a significant health issue in the US. Recent advances have provided for the transcatheter deployment of a prosthetic cardiac valve. Compared to traditional valve replacement surgery which used an "open heart" surgical procedure and typically carries a 1-4% mortality risk in otherwise healthy persons, transcatheter deployment significantly reduces morbidity as well as reducing the cost of valve replacement therapy.

While replacement of the aortic valve in a transcatheter manner has been the subject of intense investigation, lesser attention has been focused on the mitral valve. This is in part reflective of the greater level of complexity associated to the native mitral valve apparatus and thus a greater level of difficulty with regards to inserting and anchoring the replacement prosthesis.

Several designs for catheter-deployed (transcatheter) aortic valve replacement are under various stages of development. The Edwards SAPIEN transcatheter heart valve is currently undergoing clinical trial in patients with calcific aortic valve disease who are considered high-risk for conventional open-heart valve surgery. This valve is deployable via a retrograde transarterial (transfemoral) approach or an antegrade transapical (transventricular) approach. A key aspect of the Edwards SAPIEN and other transcatheter aortic valve replacement designs is their dependence on lateral fixation (e.g. tines) that engages the valve tissues as the primary anchoring mechanism. Such a design basically relies on circumferential friction around the valve housing or stent to prevent dislodgement during the cardiac cycle. This anchoring mechanism is facilitated by, and may somewhat depend on, a calcified aortic valve annulus. This design also requires that the valve housing or stent have a certain degree of rigidity.

At least one transcatheter mitral valve design is currently in development. The Endo-valve uses a folding tripod-like design that delivers a tri-leaflet bioprosthetic valve. It is designed to be deployed from a minimally invasive transatrial approach, and could eventually be adapted to a transvenous atrial septotomy delivery. This design uses "proprietary gripping features" designed to engage the valve annulus and leaflets tissues. Thus the anchoring mechanism of this device is essentially equivalent to that used by transcatheter aortic valve replacement designs.

However, such designs still pose many unsolved problems such as heart remodelling, perivalvular leaking, inability to avoid fatigue failures, clotting, tissue damage, and so on. Accordingly, improvements are needed to address these and related problems in the art.

BRIEF SUMMARY OF THE INVENTION

The present invention relates to the design and function of a single-tether compressible prosthetic heart valve replacement which can be deployed into a closed beating heart using a transcatheter delivery system. The design as discussed focuses on the deployment of a device via a minimally invasive fashion and by way of example considers a minimally invasive surgical procedure utilizing the intercostal or subxyphoid space for valve introduction. In order to accomplish this, the valve is formed in such a manner that it can be compressed to fit within a delivery system and secondarily ejected from the delivery system into the target location, for example the mitral or tricuspid valve annulus.

In a preferred embodiment, there is provided a method of tethering a prosthetic heart valve during a transcatheter valve replacement procedure comprising the step of deploying a transcatheter prosthetic heart valve in a patient using as an anchor a single tether that is anchored within the heart between an apically affixed epicardial fastening device and a stent-based fastening system, wherein the transcatheter prosthetic heart valve comprises an expandable tubular stent having a cuff and an expandable internal leaflet assembly, wherein said cuff is comprised of wire covered with stabilized tissue or synthetic material, and wherein said leaflet assembly is disposed within the stent and is comprised of stabilized tissue or synthetic material.

In another preferred embodiment, there is provided wherein the prosthetic heart valve is tethered to the apex of the left venticle using an interlocking tethering system comprised of a stent-based component and a single-tether distal component that cooperatively engages with the stent-based component to form a secure attachment of the prosthetic heart valve to the apex, and a single-tether proximal component that comprises or attaches to an epicardial tether securing device.

In another preferred embodiment, there is provided method of treating mitral or tricuspid regurgitation in a patient, which comprises the step of surgically deploying a single-tethered prosthetic heart valve into the mitral or tricuspid annulus of the patient.

In another preferred embodiment, the space between the cuff tissue and cuff dacron liner (inside-outside) may be used to create a cuff that is expandable, swellable or may be inflated and which provides an enhanced level of sealing of the cuff against the atrial trabeculations and annular tissue.

BRIEF DESCRIPTION OF THE DRAWINGS

The attached figures provide enabling and non-limiting example of certain features of the present invention. The figures are not intended to be limiting in any way to limit the description that is provided in the text.

FIG. 10 shows a three (3) connection stent-tether system with three (3) tethers connected to the stent body and converging to a polymeric intra-ventricular connecting ring. The ventricular tether is in this embodiment actually two (2) ventricular tethers, both connected to the connecting ring, and both tethers attached to the apical epicardial securing device.

FIG. 11 shows a three (3) connection stent-tether system with three (3) tethers connected to the stent body and converging to a polymeric intra-ventricular connecting ring. The ventricular tether is in this embodiment is a single (1) tether and is connecting the connecting ring to the apical epicardial securing device.

DETAILED DESCRIPTION OF THE INVENTION

Figure 1A:
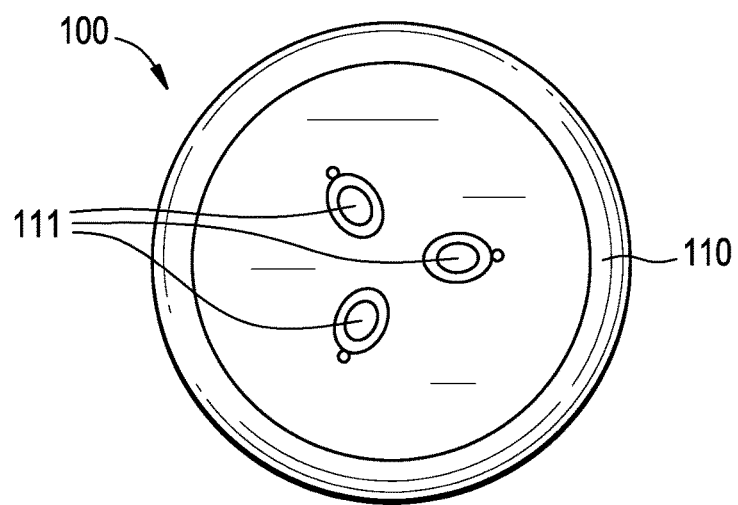
FIG. 1 is an illustration of one embodiment of an epicardial tether securing device.
FIG. 1B shows an exploded side view of the device with the pinning structure and the plug-locking structure that fits into the securement disc.
FIG. 1C shows a perspective view of the same device.

The present invention addresses problems concerning valve delivery and deployment, valve compliance, perivalvular leaking, hemodynamic issues such as LVOT and clotting, cardiac remodelling and so forth.

The present invention provides in one embodiment a tethering system for a prosthetic mitral valve that is designed to maintain integrity out to about 800 million cycles, or about 20 years. The use of a compressible prosthetic valve delivered via transcatheter endoscope techniques addresses the delivery issues. Deployment is addressed through the use of a prosthetic valve having a shape that features a tubular stent body that contains leaflets and an atrial cuff. This allows the valve to seat within the mitral annulus and be held by the native mitral leaflets. The use of a flexible valve attached using an apical tether provides compliance with the motion and geometry of the heart. The geometry and motion of the heart are well-known as exhibiting a complicated biphasic left ventricular deformation with muscle thickening and a sequential twisting motion. The additional use of the apically secured ventricular tether helps maintain the prosthetic valve's annular position without allowing the valve to migrate, while providing enough tension between the cuff and the atrial trabeculations to reduce and eliminate perivalvular leaking. The use of a single tether or a single paired-tether that is attached to a single apical location reduces or even eliminates the cardiac muscle remodelling that has been witnessed in prior art devices. These prior art devices were known to have a problem with unwanted change in tissue at the anchoring locations as well as heart-generated migration of the original anchoring locations to new locations that reduce or destroy the prior art valve's effectiveness. The use of a compliant valve prosthesis and the special shape and features help reduce or eliminate clotting and hemodynamic issues, including left ventricular outflow tract (LVOT) interference problems. Many prior art valves were not even aware of or were not able to address problems with blood flow and aorta/aortic valve compression issues.

Structurally, the prosthetic heart valve comprises a self-expanding tubular stent having a cuff at one end and tether loops for attaching tethers at the other end, and disposed within the tubular stent is a leaflet assembly that contains the valve leaflets, the valve leaflets being formed from stabilized tissue or other suitable biological or synthetic material. In one embodiment, the leaflet assembly may even include a wire form where a formed wire structure is used in conjunction with stabilized tissue to create a leaflet support structure which can have anywhere from 1, 2, 3 or 4 leaflets, or valve cusps disposed therein. In another embodiment, the leaflet assembly is wireless and uses only the stabilized tissue and stent body to provide the leaflet support structure, without using wire, and which can also have anywhere from 1, 2, 3 or 4 leaflets, or valve cusps disposed therein.

The upper cuff portion may be formed by heat-forming a portion of a tubular nitinol braided (or similar) stent such that the lower portion retains the tubular shape but the upper portion is opened out of the tubular shape and expanded to create a widened collar structure that may be shaped in a variety of functional regular or irregular funnel-like or collar-like shapes. In one preferred embodiment, the entire structure is formed from a laser-cut stent and collar design, as described further herein.

Functions of the Cuff

The cuff functions in a variety of ways. The first function of the cuff is to inhibit perivalvular leak/regurgitation of blood around the prosthesis. By flexing and sealing across the irregular contours of the annulus and atrium, leaking is minimized and/or prevented.

The second function of the cuff is to provide an adjustable and/or compliant bioprosthetic valve. The heart and its structures undergo complex conformational changes during the cardiac cycle. For example, the mitral valve annulus has a complex geometric shape known as a hyperbolic paraploid much like a saddle, with the horn being anterior, the seat back being posterior, and the left and right valleys located medially and laterally. Beyond this complexity, the area of the mitral annulus changes over the course of the cardiac cycle. Further, the geometry of the tricuspid valve and tricuspid annulus continues to be a topic of research, posing its own particular problems. Accordingly, compliance is a very important but unfortunately often overlooked requirement of cardiac devices. Compliance here refers to the ability of the valve to maintain structural position and integrity during the cardiac cycle. Compliance with the motion of the heart is a particularly important feature, especially the ability to provide localized compliance where the underlying surfaces are acting differently from the adjacent surfaces. This ability to vary throughout the cardiac cycle allows the valve to remain seated and properly deployed in a manner not heretofore provided.

Additionally, compliance may be achieved through the use of the tethers where the tethers are preferably made from an elastic material. Optionally, tethers may be made from polymer filaments known in the surgical field and exhibiting strength and resilience properties adequate for valve stabilization. Tether-based compliance may be used alone, or in combination with the cuff-based compliance.

The third function of the cuff valve is to provide a valve that, during surgery, is able to be seated and be able to contour to the irregular surfaces of the atrium. The use of independent tethers allows for side to side fitting of the valve within the annulus. For example, where three tethers are used, they are located circumferentially about 120 degrees relative to each other which allows the surgeon to observe whether or where perivalvular leaking might be occurring and to pull on one side or the other to create localized pressure and reduce or eliminate the leaking.

The forth function of the cuff is to counter the forces that act to displace the prosthesis toward/into the ventricle (i.e. atrial pressure and flow-generated shear stress) during ventricular filling.

Additional features of the cuff include that it functions to strengthen the leaflet assembly/stent combination by providing additional structure. Further, during deployment, the cuff functions to guide the entire structure, the prosthetic valve, into place at the mitral annulus during deployment and to keep the valve in place once it is deployed.

Cuff Structure

The cuff is a substantially flat plate that projects beyond the diameter of the tubular stent to form a rim or border. As used herein, the term cuff, flange, collar, bonnet, apron, or skirting are considered to be functionally equivalent. When the tubular stent is pulled through the mitral valve aperture, the mitral annulus, by the tether loops in the direction of the left ventricle, the cuff acts as a collar to stop the tubular stent from traveling any further through the mitral valve aperture. The entire prosthetic valve is held by longitudinal forces between the cuff which is seated in the left atrium and mitral annulus, and the ventricular tethers attached to the left ventricle.

The cuff is formed from a stiff, flexible shape-memory material such as the nickel-titanium alloy material Nitinol™ wire that is covered by stabilized tissue or other suitable biocompatible or synthetic material. In one embodiment, the cuff wire form is constructed from independent loops of wire that create lobes or segments extending axially around the circumference of the bend or seam where the cuff transitions to the tubular stent (in an integral cuff) or where the cuff is attached to the stent (where they are separate, but joined components).

Once covered by stabilized tissue or material, the loops provide the cuff the ability to travel up and down, to articulate, along the longitudinal axis that runs through the center of the tubular stent. In other words, the individual spindles or loops can independently move up and down, and can spring back to their original position due to the relative stiffness of the wire. The tissue or material that covers the cuff wire has a certain modulus of elasticity such that, when attached to the wire of the cuff, is able to allow the wire spindles to move. This flexibility gives the cuff, upon being deployed within a patient's heart, the ability to conform to the anatomical shape necessary for a particular application.

In the example of a prosthetic mitral valve, the cuff is able to conform to the irregularities of the left atrium and shape of the mitral annulus, and to provide a tight seal against the atrial tissue adjacent the mitral annulus and the tissue within the mitral annulus. As stated previously, this feature importantly provides a degree of flexibility in sizing the a mitral valve and prevents blood from leaking around the implanted prosthetic heart valve.

An additional important aspect of the cuff dimension and shape is that, when fully seated and secured, the edge of the cuff preferably should not be oriented laterally into the atrial wall such that it can produce a penetrating or cutting action on the atrial wall.

In one preferred embodiment, the wire spindles of the cuff are substantially uniform in shape and size. In another preferred embodiment of the present invention, each loop or spindle may be of varying shapes and sizes. In this example, it is contemplated that the loops may form a pattern of alternating large and small loops, depending on where the valve is being deployed. In the case of a prosthetic mitral valve, pre-operative imaging may allow for customizing the structure of the cuff depending on a particular patient's anatomical geometry in the vicinity of the mitral annulus.

The cuff wire form is constructed so as to provide sufficient structural integrity to withstand the intracardiac forces without collapsing. The cuff wire form is preferably constructed of a superelastic metal, such as Nitinol™ and is capable of maintaining its function as a sealing collar for the tubular stent while under longitudinal forces that might cause a structural deformation or valve displacement. It is contemplated as within the scope of the invention to optionally use other shape memory alloys such as Cu—Zn—Al—Ni alloys, and Cu—Al—Ni alloys. The heart is known to generate an average left atrial pressure between about 8 and 30 mm Hg (about 0.15 to 0.6 psi). This left atrial filling pressure is the expected approximate pressure that would be exerted in the direction of the left ventricle when the prosthesis is open against the outer face of the cuff as an anchoring force holding the cuff against the atrial tissue that is adjacent the mitral valve. The cuff counteracts this longitudinal pressure against the prosthesis in the direction of the left ventricle to keep the valve from being displaced or slipping into the ventricle. In contrast, left ventricular systolic pressure, normally about 120 mm Hg, exerts a force on the closed prosthesis in the direction of the left atrium. The tethers counteract this force and are used to maintain the valve position and withstand the ventricular force during ventricular contraction or systole. Accordingly, the cuff has sufficient structural integrity to provide the necessary tension against the tethers without being dislodged and pulled into the left ventricle. After a period of time, changes in the geometry of the heart and/or fibrous adhesion between prosthesis and surrounding cardiac tissues may assist or replace the function of the ventricular tethers in resisting longitudinal forces on the valve prosthesis during ventricular contraction.

Stent Structure

Preferably, superelastic metal wire, such as Nitinol™ wire, is used for the stent, for the inner wire-based leaflet assembly that is disposed within the stent, and for the cuff wire form. As stated, it is contemplated as within the scope of the invention to optionally use other shape memory alloys such as Cu—Zn—Al—Ni alloys, and Cu—Al—Ni alloys. It is contemplated that the stent may be constructed as a braided stent or as a laser cut stent. Such stents are available from any number of commercial manufacturers, such as Pulse Systems. Laser cut stents are preferably made from Nickel-Titanium (Nitinol™), but also without limitation made from stainless steel, cobalt chromium, titanium, and other functionally equivalent metals and alloys, or Pulse Systems braided stent that is shape-set by heat treating on a fixture or mandrel.

One key aspect of the stent design is that it be compressible and when released have the stated property that it return to its original (uncompressed) shape. This requirement limits the potential material selections to metals and plastics that have shape memory properties. With regards to metals, Nitinol has been found to be especially useful since it can be processed to be austhenitic, martensitic or super elastic. Martensitic and super elastic alloys can be processed to demonstrate the required compression features.

Laser Cut Stent

One possible construction of the stent envisions the laser cutting of a thin, isodiametric Nitinol tube. The laser cuts form regular cutouts in the thin Nitinol tube. Secondarily the tube is placed on a mold of the desired shape, heated to the Martensitic temperature and quenched. The treatment of the stent in this manner will form a stent or stent/cuff that has shape memory properties and will readily revert to the memory shape at the calibrated temperature.

Braided Wire Stent

A stent can be constructed utilizing simple braiding techniques. Using a Nitinol wire—for example a 0.012" wire—and a simple braiding fixture, the wire is wound on the braiding fixture in a simple over/under braiding pattern until an isodiametric tube is formed from a single wire. The two loose ends of the wire are coupled using a stainless steel or Nitinol coupling tube into which the loose ends are placed and crimped. Angular braids of approximately 60 degrees have been found to be particularly useful. Secondarily, the braided stent is placed on a shaping fixture and placed in a muffle furnace at a specified temperature to set the stent to the desired shape and to develop the martensitic or super elastic properties desired.

The stent as envisioned in one preferred embodiment is designed such that the ventricular aspect of the stent comes to 2-5 points onto which anchoring sutures are affixed. The anchoring sutures (tethers) will traverse the ventricle and ultimately be anchored to the epicardial surface of the heart approximately at the level of the apex. The tethers when installed under slight tension will serve to hold the valve in place, i.e. inhibit paravalvular leakage during systole.

Leaflet and Assembly Structure

The valve leaflets are held by, or within, a leaflet assembly. In one preferred embodiment of the invention, the leaflet assembly comprises a leaflet wire support structure to which the leaflets are attached and the entire leaflet assembly is housed within the stent body. In this embodiment, the assembly is constructed of wire and stabilized tissue to form a suitable platform for attaching the leaflets. In this aspect, the wire and stabilized tissue allow for the leaflet structure to be compressed when the prosthetic valve is compressed within the deployment catheter, and to spring open into the proper functional shape when the prosthetic valve is opened during deployment. In this embodiment, the leaflet assembly may optionally be attached to and housed within a separate cylindrical liner made of stabilized tissue or material, and the liner is then attached to line the interior of the stent body.

In this embodiment, the leaflet wire support structure is constructed to have a collapsible/expandable geometry. In a preferred embodiment, the structure is a single piece of wire. The wireform is, in one embodiment, constructed from a shape memory alloy such as Nitinol. The structure may optionally be made of a plurality of wires, including between 2 to 10 wires. Further, the geometry of the wire form is without limitation, and may optionally be a series of parabolic inverted collapsible arches to mimic the saddle-like shape of the native annulus when the leaflets are attached. Alternatively, it may optionally be constructed as collapsible concentric rings, or other similar geometric forms that are able to collapse/compress which is followed by an expansion to its functional shape. In certain preferred embodiments, there may be 2, 3 or 4 arches. In another embodiment, closed circular or ellipsoid structure designs are contemplated. In another embodiment, the wire form may be an umbrella-type structure, or other similar unfold-and-lock-open designs. A preferred embodiment utilizes super elastic Nitinol wire approximately 0.015" in diameter. In this embodiment, the wire is wound around a shaping fixture in such a manner that 2-3 commissural posts are formed. The fixture containing the wrapped wire is placed in a muffle furnace at a pre-determined temperature to set the shape of the wire form and to impart it's super elastic properties. Secondarily, the loose ends of the wireform are joined with a stainless steel or Nitinol tube and crimped to form a continuous shape. In another preferred embodiment, the commissural posts of the wireform are adjoined at their tips by a circular connecting ring, or halo, whose purpose is to minimize inward deflection of the post(s).

In another preferred embodiment, the leaflet assembly is constructed solely of stabilized tissue or other suitable material without a separate wire support structure. The leaflet assembly in this embodiment is also disposed within the lumen of the stent and is attached to the stent to provide a sealed joint between the leaflet assembly and the inner wall of the stent. By definition, it is contemplated within the scope of the invention that any structure made from stabilized tissue and/or wire(s) related to supporting the leaflets within the stent constitute a leaflet assembly.

In this embodiment, stabilized tissue or suitable material may also optionally be used as a liner for the inner wall of the stent and is considered part of the leaflet assembly.

Liner tissue or biocompatible material may be processed to have the same or different mechanical qualities, e.g. thickness, durability, etc. from the leaflet tissue.

Deployment within the Valvular Annulus

The prosthetic heart valve is, in one embodiment, apically delivered through the apex of the left ventricle of the heart using a catheter system. In one aspect of the apical delivery, the catheter system accesses the heart and pericardial space by intercostal delivery. In another delivery approach, the catheter system delivers the prosthetic heart valve using either an antegrade or retrograde delivery approach using a flexible catheter system, and without requiring the rigid tube system commonly used. In another embodiment, the catheter system accesses the heart via a trans-septal approach.

In one non-limiting preferred embodiment, the stent body extends into the ventricle about to the edge of the open mitral valve leaflets (approximately 25% of the distance between the annulus and the ventricular apex). The open native leaflets lay against the outside stent wall and parallel to the long axis of the stent (i.e. the stent holds the native mitral valve open).

In one non-limiting preferred embodiment, the diameter should approximately match the diameter of the mitral annulus. Optionally, the valve may be positioned to sit in the mitral annulus at a slight angle directed away from the aortic valve such that it is not obstructing flow through the aortic valve. Optionally, the outflow portion (bottom) of the stent should not be too close to the lateral wall of the ventricle or papillary muscle as this position may interfere with flow through the prosthesis. As these options relate to the tricuspid, the position of the tricuspid valve may be very similar to that of the mitral valve.

In another embodiment, the prosthetic valve is sized and configured for use in areas other than the mitral annulus, including, without limitation, the tricuspid valve between the right atrium and right ventricle. Alternative embodiments may optionally include variations to the cuff structure to accommodate deployment to the pulmonary valve between the right ventricle and pulmonary artery, and the aortic valve between the left ventricle and the aorta. In one embodiment, the prosthetic valve is optionally used as a venous backflow valve for the venous system, including without limitation the vena cava, femoral, subclavian, pulmonary, hepatic, renal and cardiac. In this aspect, the cuff feature is utilized to provide additional protection against leaking.

Anchoring Tether, Tether Bundle, Positioning Tethers

In one preferred embodiment of the present invention, there is a tether-bundle that attaches to the extended points (two or three or four) of the stent and which converge to a central nexus point, to which the single tether is attached and leads to the apical tissue anchor location within the heart. In one preferred embodiment, the tether extends downward through the left ventricle, exiting the left ventricle at the apex of the heart to be fastened on the epicardial surface outside of the heart. Similar anchoring is contemplated herein as it regards the tricuspid, or other valve structure requiring a prosthetic.

In another preferred embodiment, there may be additional positioning-tethers optionally be attached to the cuff to provide additional control over position, adjustment, and compliance during deployment and possible for up to 30 days afterwards to ensure there is no leaking. It is contemplated that the positioning tethers may be kept and gathered outside of the patient body for a period of time until the interventionist can verify by Echocardiography or Fluoroscopy that no further adjustment is necessary. In this preferred embodiment, one or more tethers are optionally attached to the cuff, in addition to, or optionally, in place of, the tethers attached to the stent. By attaching to the cuff and/or the stent, an even higher degree of control over positioning, adjustment, and compliance is provided to the operator during deployment.

During deployment, the operator is able to adjust or customize the tethers to the correct length for a particular patient's anatomy. The tethers also allow the operator to tighten the cuff onto the tissue around the valvular annulus by pulling the tethers, which creates a leak-free seal.

In another preferred embodiment, the tethers are optionally anchored to other tissue locations depending on the particular application of the prosthetic heart valve. In the case of a mitral valve, or the tricuspid valve, there are optionally one or more tethers anchored to one or both papillary muscles, septum, and/or ventricular wall.

The tethers, in conjunction with the cuff, provide for a compliant valve which has heretofore not been available. The tethers are made from surgical-grade materials such as biocompatible polymer suture material. Examples of such material include 2-0 exPFTE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle. Upon being drawn to and through the apex of the heart, the tethers may be fastened by a suitable mechanism such as tying off to a pledget or similar adjustable button-type anchoring device to inhibit retraction of the tether back into the ventricle. It is also contemplated that the tethers might be bioresorbable/bioabsorbable and thereby provide temporary fixation until other types of fixation take hold such a biological fibrous adhesion between the tissues and prosthesis and/or radial compression from a reduction in the degree of heart chamber dilation.

Further, it is contemplated that the prosthetic heart valve may optionally be deployed with a combination of installation tethers and the permanent tether, attached to either the stent or cuff, or both, the installation tethers being removed after the valve is successfully deployed. It is also contemplated that combinations of inelastic and elastic tethers may optionally be used for deployment and to provide structural and positional compliance of the valve during the cardiac cycle.

Pledget

In one embodiment, to control the potential tearing of tissue at the apical entry point of the delivery system, a circular, semi-circular, or multi-part pledget is employed. The pledget may be constructed from a semi-rigid material such as PFTE felt. Prior to puncturing of the apex by the delivery system, the felt is firmly attached to the heart such that the apex is centrally located. Secondarily, the delivery system is introduced through the central area, or orifice as it may be, of the pledget. Positioned and attached in this manner, the pledget acts to control any potential tearing at the apex.

Tines/Barbs

In another embodiment the valve can be seated within the valvular annulus through the use of tines or barbs. These may be used in conjunction with, or in place of one or more tethers. The tines or barbs are located to provide attachment to adjacent tissue. In one preferred embodiment, the tines are optionally circumferentially located around the bend/transition area between the stent and the cuff. Such tines are forced into the annular tissue by mechanical means such as using a balloon catheter. In one non-limiting embodiment, the tines may optionally be semi-circular hooks that upon expansion of the stent body, pierce, rotate into, and hold annular tissue securely.

Stabilized Tissue or Biocompatible Material

In one embodiment, it is contemplated that multiple types of tissue and biocompatible material may be used to cover the cuff, to form the valve leaflets, to form a wireless leaflet assembly, and/or to line both the inner and/or outer lateral walls of the stent. As stated previously, the leaflet component may be constructed solely from stabilized tissue, without using wire, to create a leaflet assembly and valve leaflets. In this aspect, the tissue-only leaflet component may be attached to the stent with or without the use of the wire form. In a preferred embodiment, there can be anywhere from 1, 2, 3 or 4 leaflets, or valve cusps.

It is contemplated that the tissue may be used to cover the inside of the stent body, the outside of the stent body, and the top and/or bottom side of the cuff wire form, or any combination thereof.

In one preferred embodiment, the tissue used herein is optionally a biological tissue and may be a chemically stabilized valve of an animal, such as a pig. In another preferred embodiment, the biological tissue is used to make leaflets that are sewn or attached to a metal frame. This tissue is chemically stabilized pericardial tissue of an animal, such as a cow (bovine pericardium) or sheep (ovine pericardium) or pig (porcine pericardium) or horse (equine pericardium).

Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic valve for implantation, and U.S. Pat. No. 5,336,616 to LifeCell Corporation discloses acellular collagen-based tissue matrix for transplantation.

In one preferred embodiment, the valve leaflets may optionally be made from a synthetic material such a polyurethane or polytetrafluoroethylene. Where a thin, durable synthetic material is contemplated, e.g. for covering the cuff, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

In another embodiment, the valve leaflets may optionally have a surface that has been treated with (or reacted with) an anti-coagulant, such as, without limitation, immobilized heparin. Such currently available heparinized polymers are known and available to a person of ordinary skill in the art.

Alternatively, the valve leaflets may optionally be made from pericardial tissue or small intestine submucosal tissue.

Retrieval System

In another embodiment, a retrieval system is contemplated for quickly removing the prosthetic valve during an aborted surgical deployment using minimally invasive cardiac catheter techniques. In this embodiment, the tethers would be captured by a catheter having a snare attachment. Once the tethers were captured, an intra-ventricular funnel attachment would guide the prosthetic valve into a collapsed, compressed conformation by pulling on the tethers, thus pulling the compressed prosthetic valve into the removal catheter for subsequent extraction.

DESCRIPTION OF THE FIGURES

Referring now to the FIGURES, there is one embodiment of a single-tethered prosthetic heart valve according to the present invention.

Figure 1B:
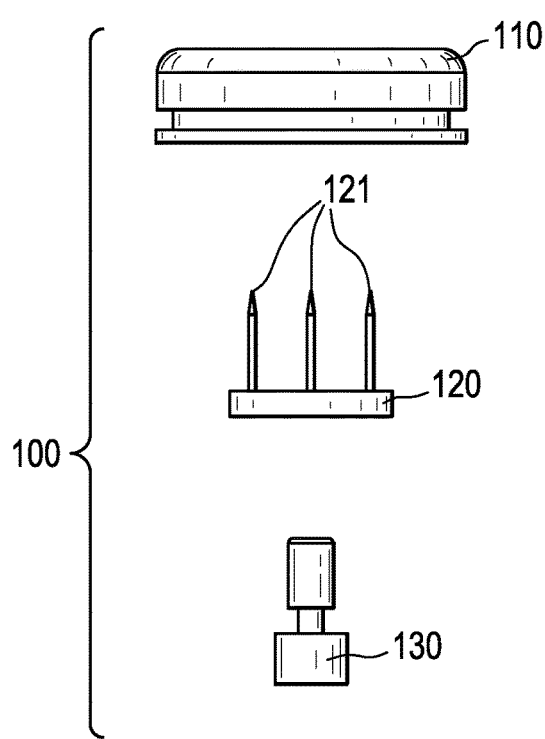
Figure 1C:
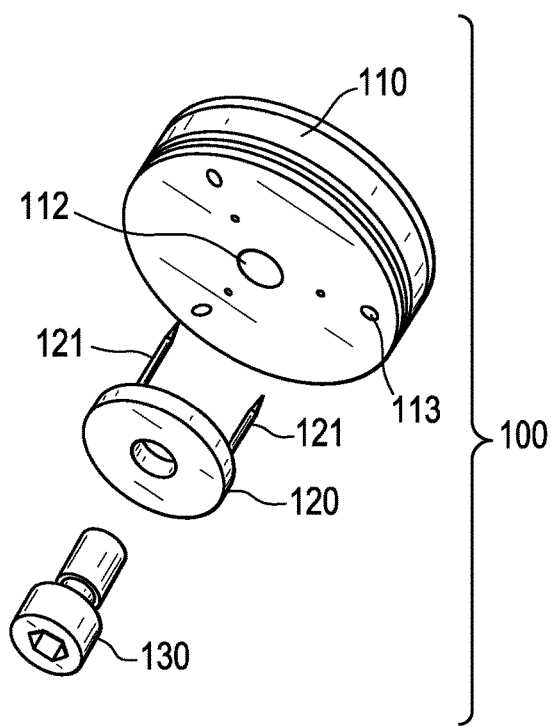

FIG. 1A shows a top view of one embodiment of a three-part epicardial tether securing device 100 wherein three tether holes 111 perforate the body of securement disc 110. FIG. 1B shows an exploded side view of the device comprising securement disc component 110, pinning component 120 and plug-locking component 120. In this view, a plurality of pins 121 extend from the body of pinning component 120 and the plug-locking component 130 is gauged to fit snugly within the center hole 122 of the pinning structure 120 and the center hole 112 of securement disc component 110, respectively. FIG. 1C shows a perspective view of the same device.

Figure 2:
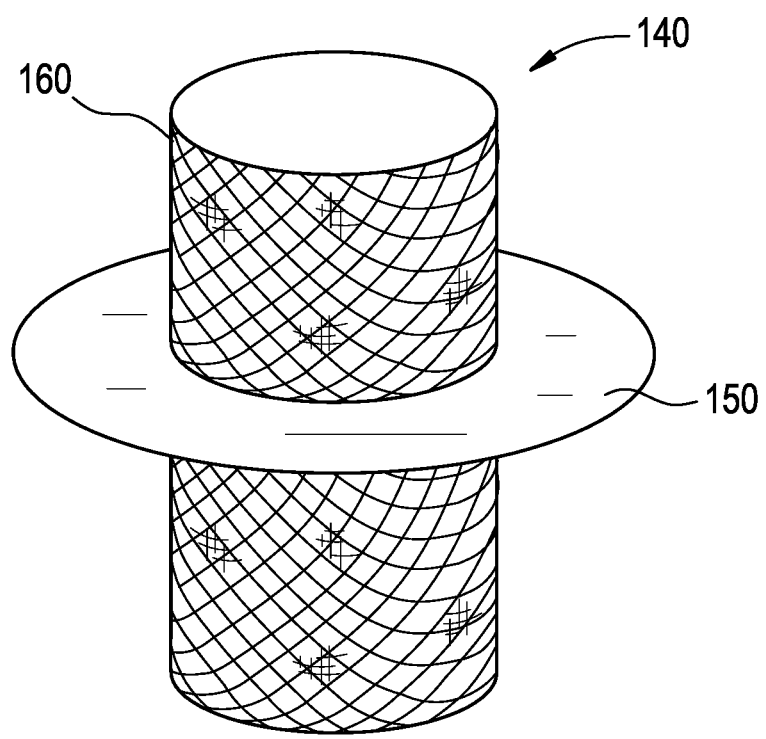
FIG. 2 is an illustration of one embodiment of the prosthetic valve of the present invention showing a mid-stent cuff design.

FIG. 2 is an illustration of one embodiment of the prosthetic valve 140 of the present invention showing a mid-stent cuff design. This design positions the top of the stent body 141 above the atrial floor at the mitral annulus, with the cuff 150 positioned over the atrial floor directly above the mitral annulus with the interior prosthetic leaflet structure (not pictured) installed at or near the top, atrial end of the stent body 160. This design necessitates the use of a laser cut stent or a combination of a braided stent and an additional fused/joined collar component.

Figure 3:
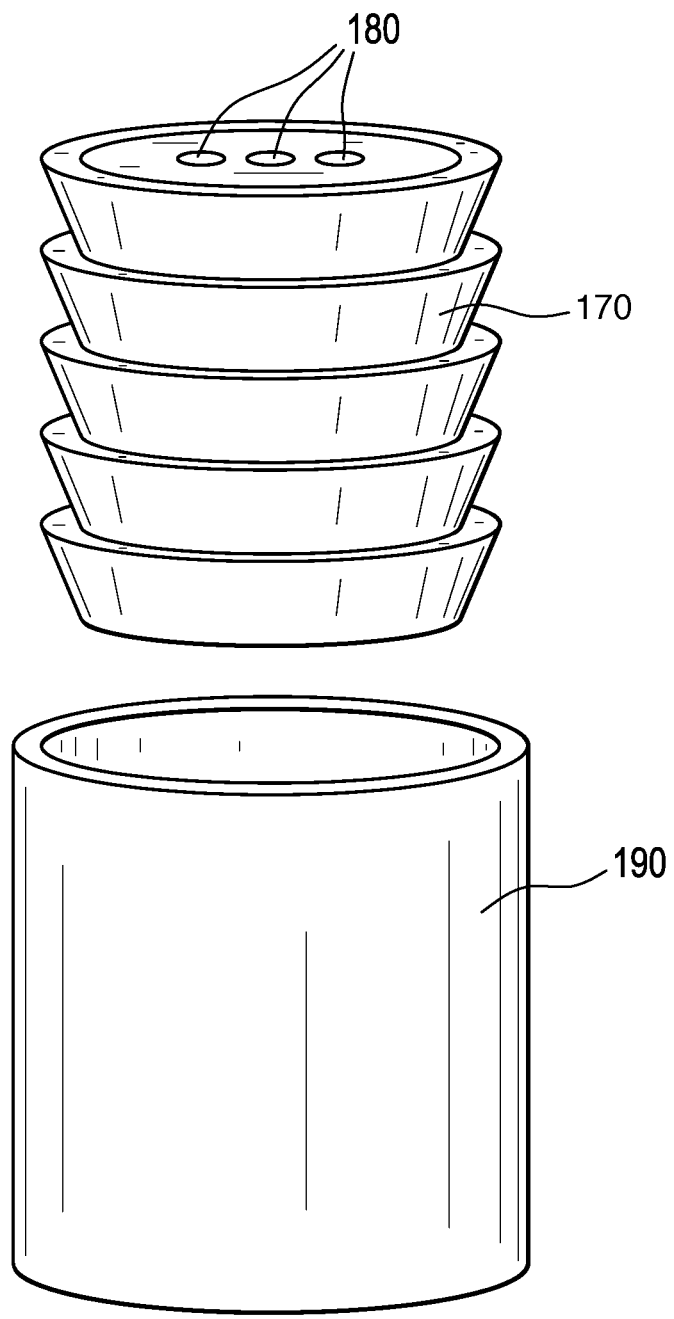
FIG. 3 is an illustration of one example of a locking tether connector having a tooth and groove design for attaching the ventricular tether to the stent body/stent-tether system.

FIG. 3 is an illustration of one example of a locking tether connector 170 having a tooth and groove design for attaching the ventricular tether to the stent body/stent-tether system. The use of a connector to attach the single ventricular tether (not pictured) to the node of the tether-bundle (not pictured) emanating from the stent body is to reduce the wear that is observed on the tethers and/or to minimize the number of perforations required in the pericardial tissue to secure the tether(s). In this embodiment, each tether emanating from the stent body extends into a tether hole 181 in the toothed component 180, which is fitted into the grooved barrel 190. The tether holes 180 converge on the interior of the toothed component 180 such that they emerge from a single tether hole (not pictured) at the bottom of such toothed component 180 as a single, braided ventricular tether (not pictured). Wear on tethers and subsequent failure is known to have catastrophic consequences and result in death of the patient, while surgical alteration of the pericardial tissue, including at the apex, is known to have the effect, over time, of causing changes to the shape of the left ventricle.

Figure 4:
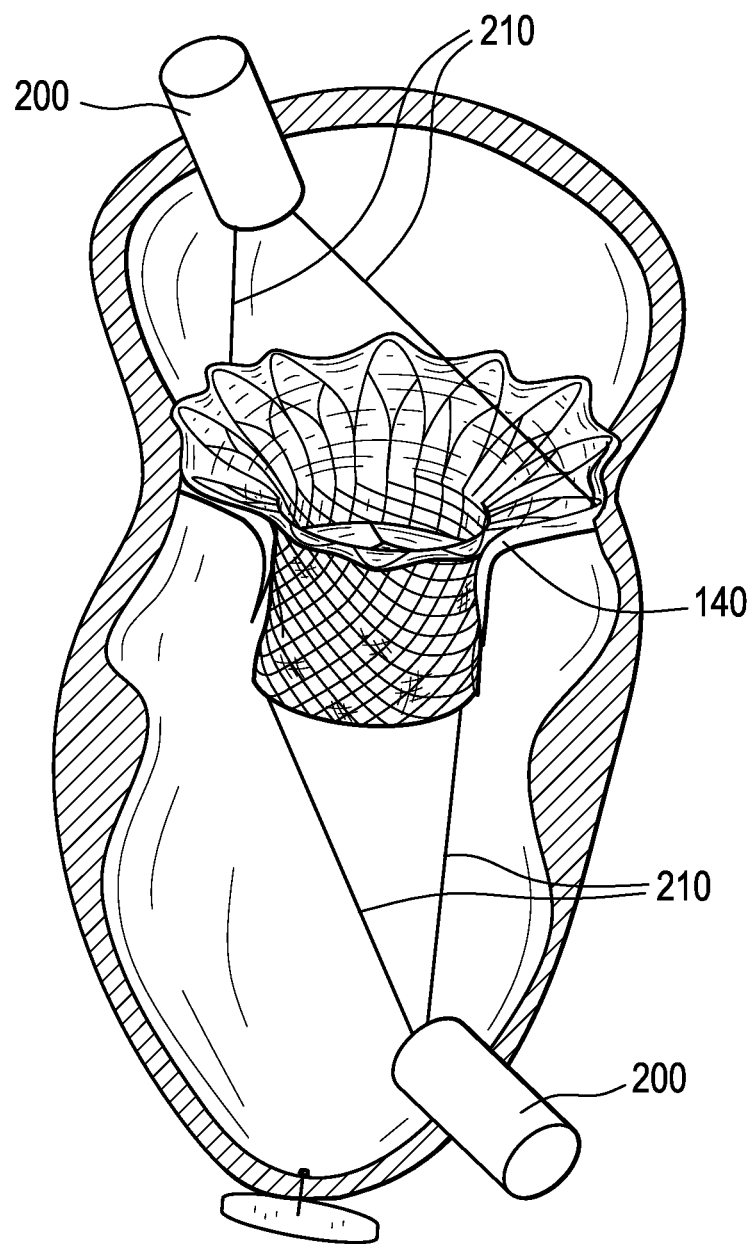
FIG. 4 is an illustration of a prosthetic mitral valve being deployed within the left atrium (upper) and the left ventricle (lower), using endoscopic catheters fitted with positioning tethers.

FIG. 4 is an illustration of a prosthetic mitral valve 140 being deployed within the left atrium (upper) and the left ventricle (lower), using endoscopic catheters 200 fitted with positioning tethers 210.

Figure 5:
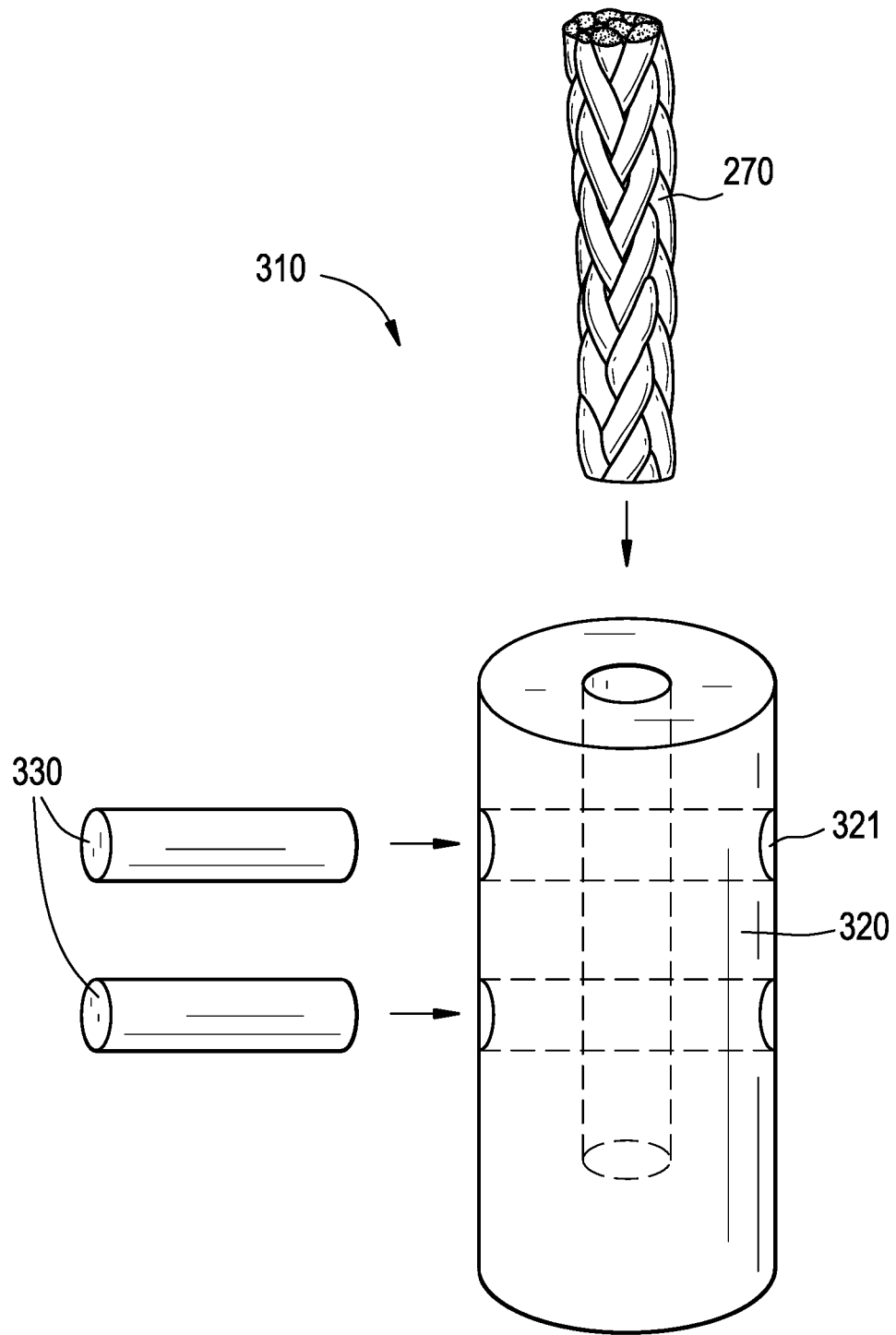
FIG. 5 is an illustration of a two-way locking peg system for attaching the ventricular tether to the stent body/stent-tether system.

FIG. 5 is an illustration of a two-way locking peg system 310 for attaching the single ventricular tether 270 to the epicardial securing device 100. In the pictured embodiment, the tip of the braided single ventricular tether 270, having passed through the epicardial securing device (not pictured), is inserted into cap component 320. Pins 330 are then placed all the way through cap holes 321, and are thusly passed through the braided filaments of tether 270 to hold such tether in place. Again, the use of a connector to attach the single ventricular tether to the node of the tether-bundle hanging from the stent body is to reduce the wear that is observed on the tethers, and avoid catastrophic device failure and death of the patient.

Figure 6:
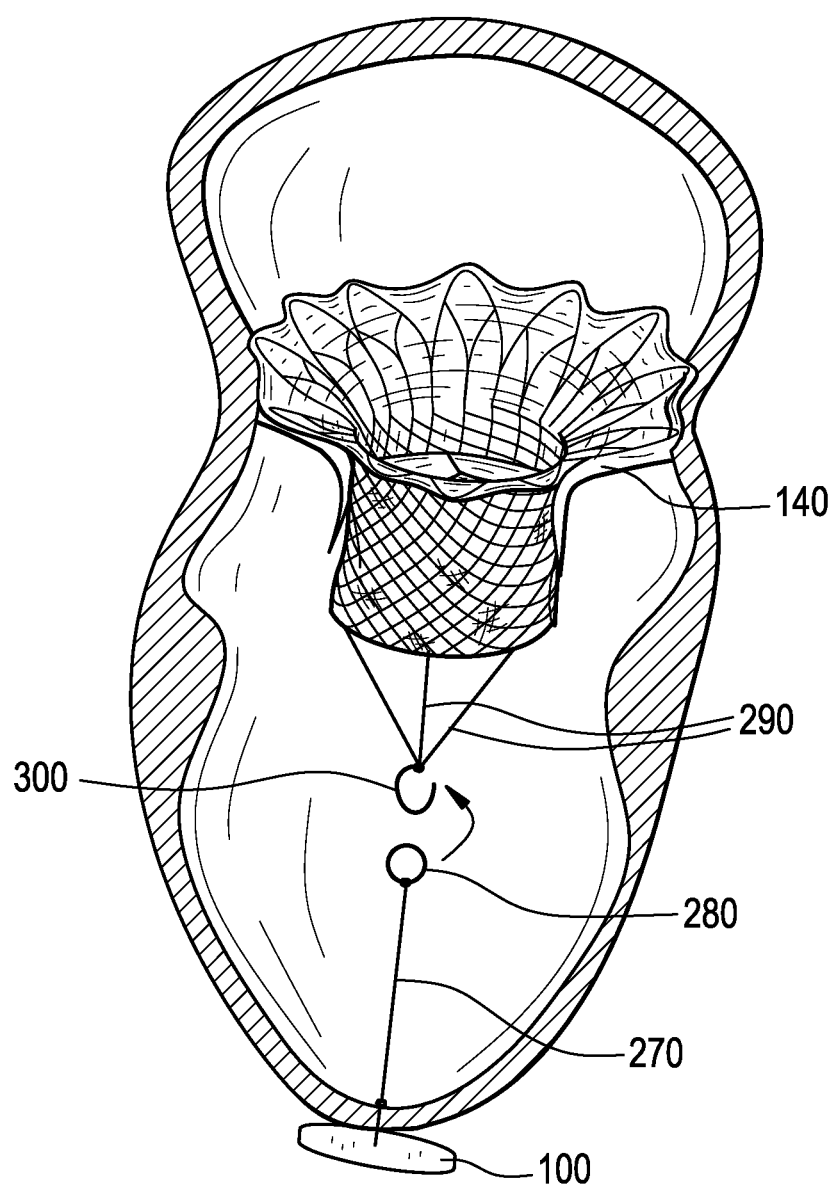
FIG. 6 is an illustration of one example of a single tether embodiment having an epicardial securing device at the apex connecting the single ventricular tether to a stent-tethering system of centering tethers.

FIG. 6 is an illustration of one example of a single tether embodiment having the epicardial tether securing device 100 at the apex connecting the single ventricular tether 270 to a stent-tethering system of centering tethers. In this embodiment, the single ventricular tether 270 is tied to a single tether loop 280 at one end and secured to the epicardial tether securing device 100 at its other end, while the centering tethers 290 emanating from the stent body 160 are tied at a central point to a stent tether loop 300, such stent tether loop remaining open until secured through single tether loop 280 during installation of the valve.

Figure 7:
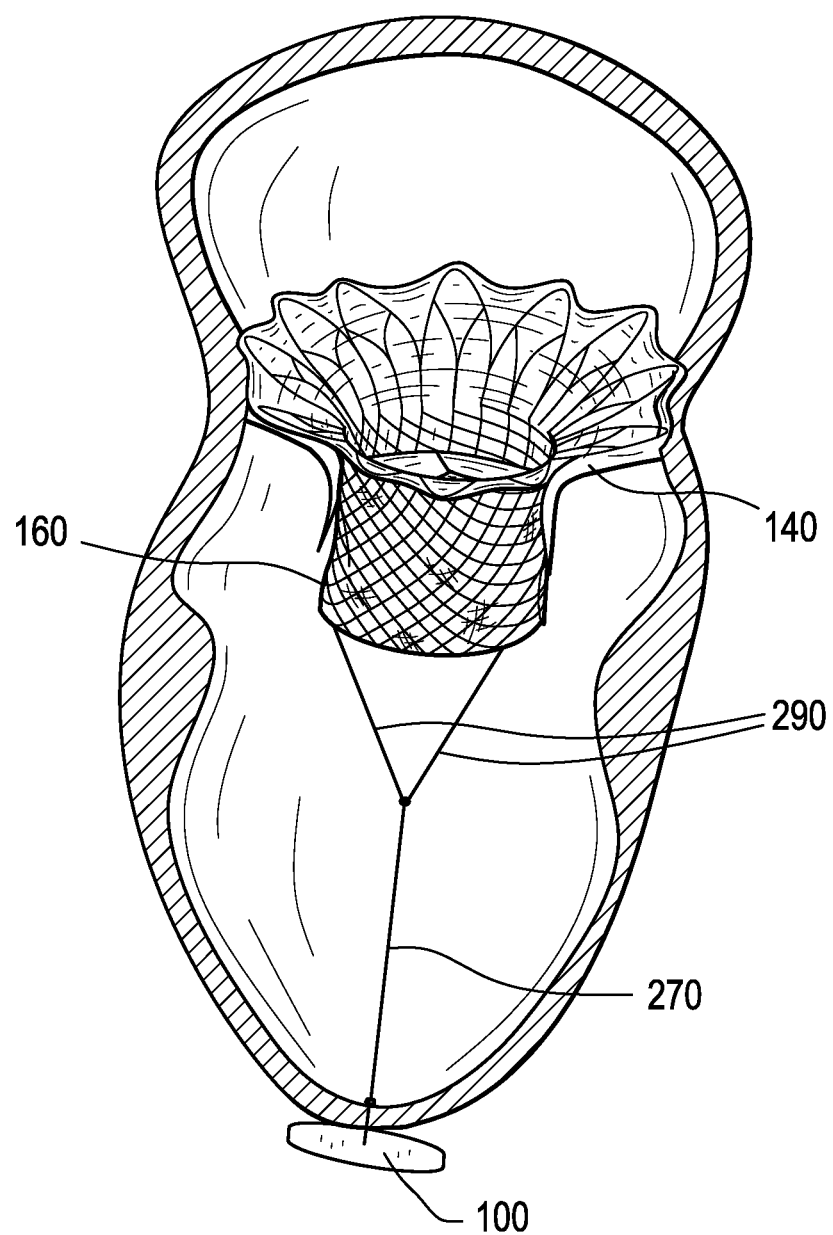
FIG. 7 is an illustration of a prosthetic valve having a single ventricular tether connected to the stent body via a stent-tether system having two (2) centering tethers attached to the stent body portion of the valve.

FIG. 7 is an illustration of a prosthetic valve 140 having a single ventricular tether 270 connected to the stent body portion of the valve 160 via a stent-tether system having two (2) centering tethers 290 attached to the stent body 160, with the single ventricular tether 270 attached on its other end to the epicardial tether securing device 100.

Figure 8:
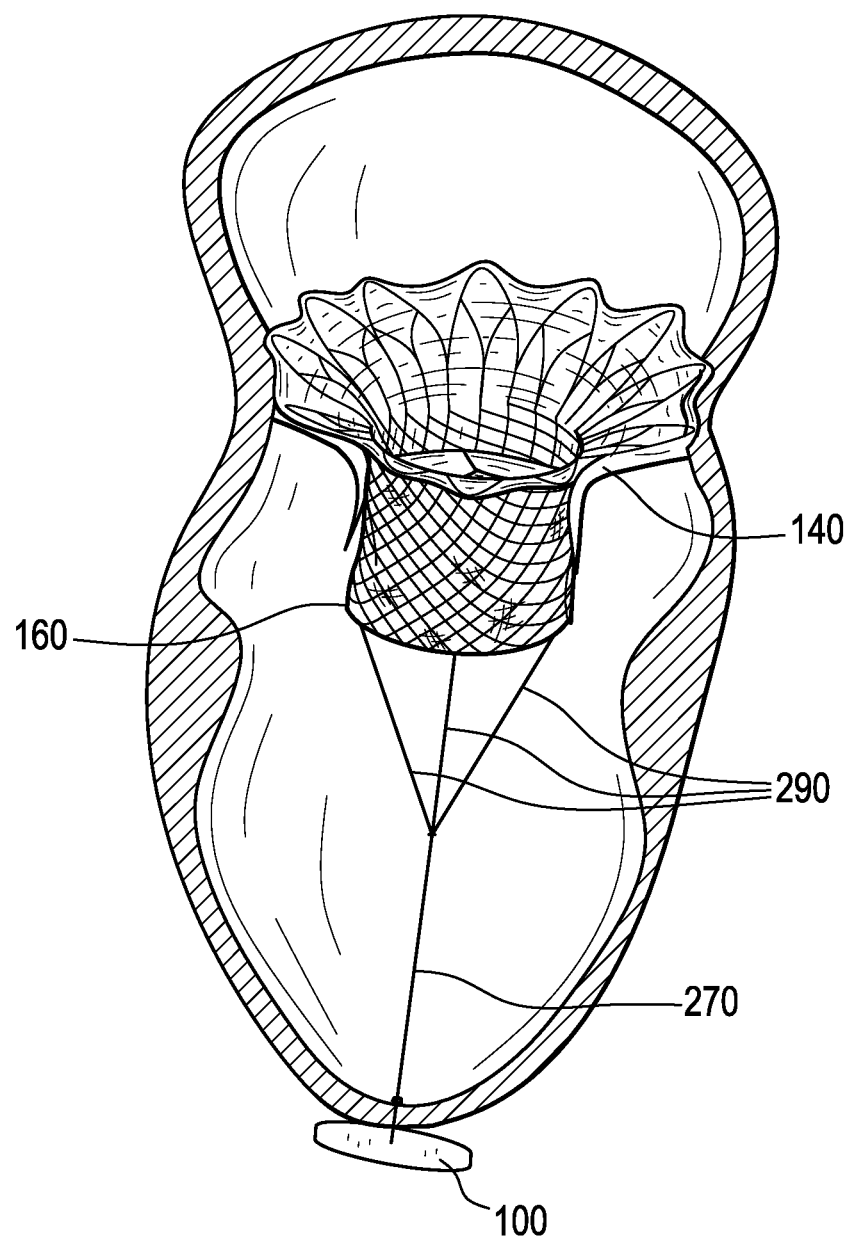
FIG. 8 is an illustration of a prosthetic valve having a single ventricular tether connected to the stent body via a stent-tether system having three (3) centering tethers attached to the stent body portion of the valve.
Figure 9:
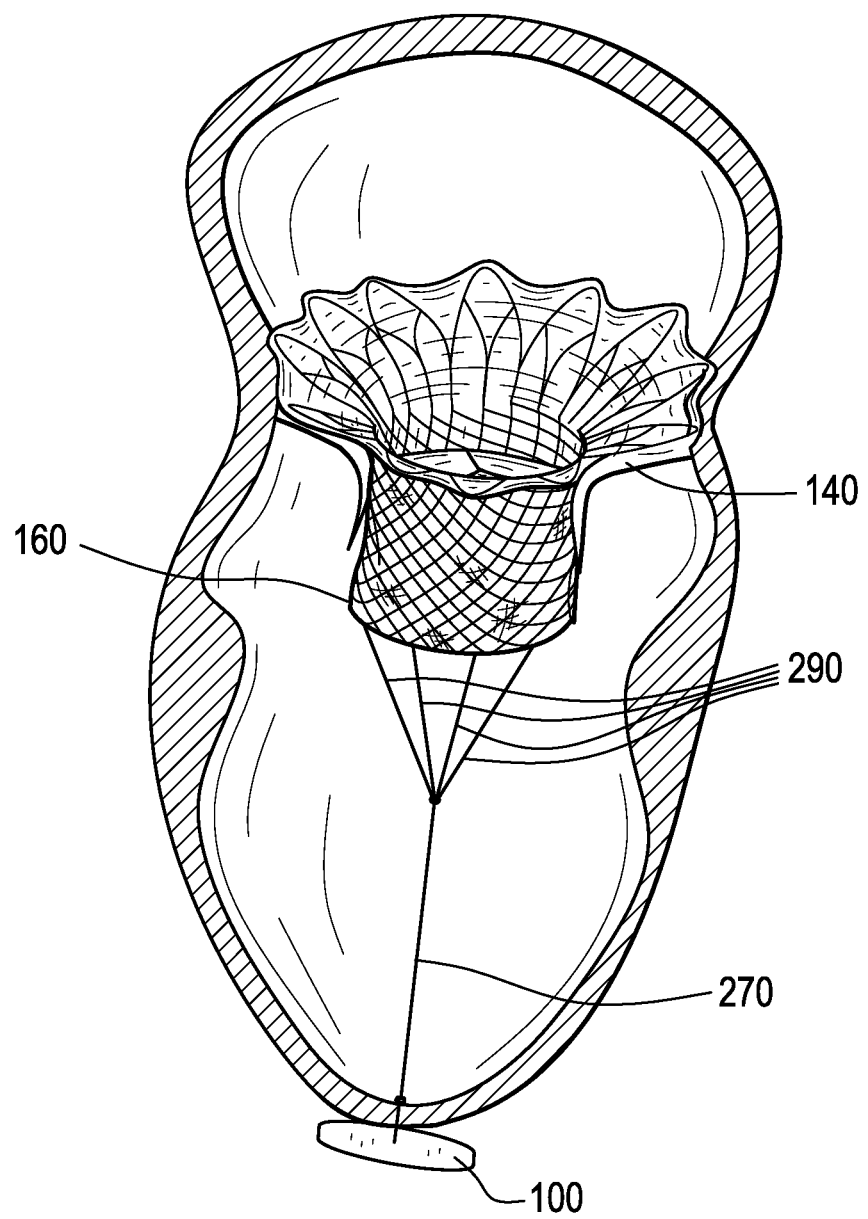
FIG. 9 is an illustration of a prosthetic valve having a single ventricular tether connected to the stent body via a stent-tether system having four (4) centering tethers attached to the stent body portion of the valve.

FIG. 8 is an illustration of a prosthetic valve 140 having a single ventricular tether 270 connected to the stent body portion of the valve 160 via a stent-tether system having three (3) centering tethers 290 attached to the stent body 160, with the single ventricular tether attached on its other end to the epicardial tether securing device 100. FIG. 9 is an illustration of a prosthetic valve 140 having a single ventricular tether 270 connected to the stent body portion of the valve 160 via a stent-tether system having four (4) centering tethers 290 attached to the stent body 160, with the single ventricular tether attached on its other end to the epicardial tether securing device 100.

In each embodiment of FIGS. 7-9, centering tethers 290 are either tied to single ventricular tether 270, or are braided together to form single ventricular tether 270.

Figure 10:
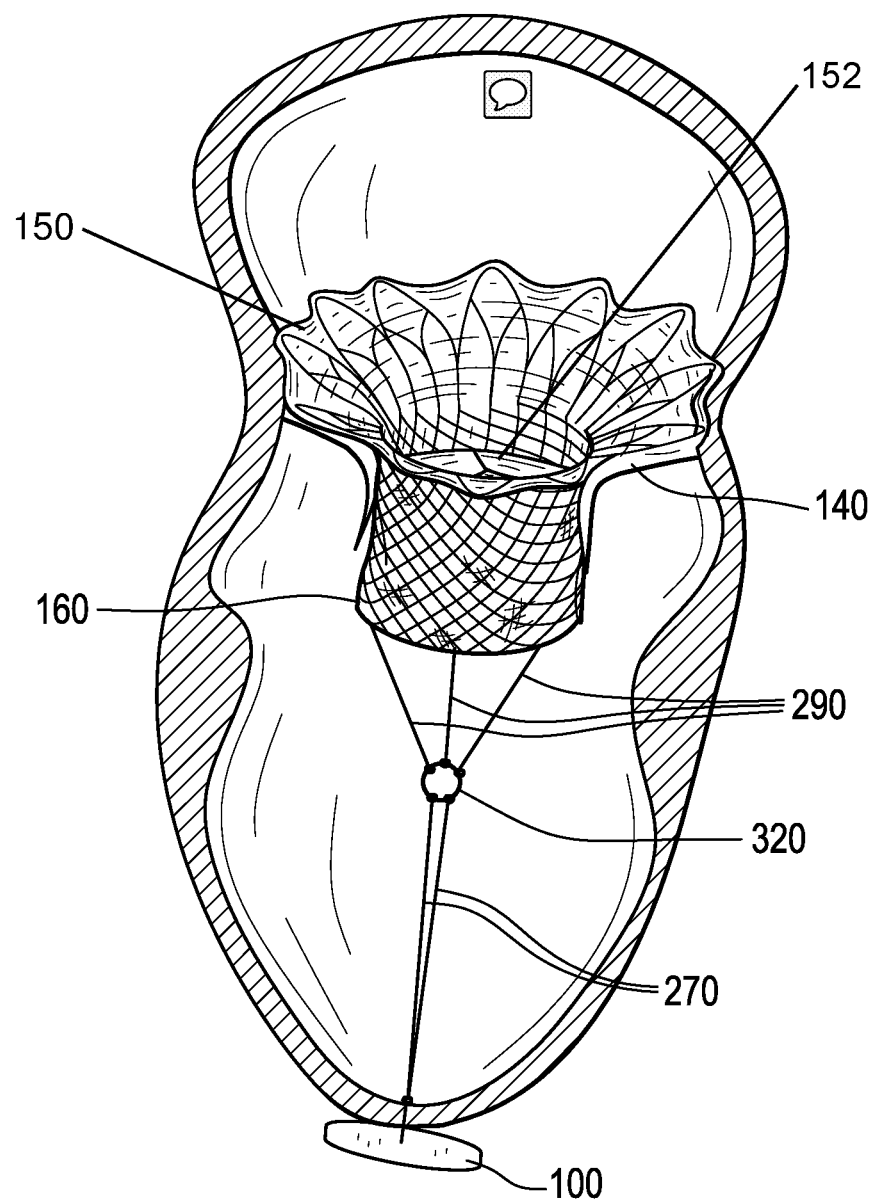
FIG. 10 is an illustration of a prosthetic mitral valve deployed within the mitral annulus with the upper cuff located in the left atrium and lower stent body in or towards the left ventricle.

FIG. 10 is an illustration of a prosthetic mitral valve 140 deployed within the mitral annulus with the upper cuff 150 and leaflet assembly 152 located in the left atrium and lower stent body 160 in or towards the left ventricle. FIG. 10 shows a three (3) connection stent-tether system with three (3) centering tethers 290 connected to the stent body 160 and converging to a polymeric intraventricular connecting ring 320. The ventricular tether 270 is in this embodiment actually two (2) ventricular tethers, both connected to the connecting ring 320, and both ventricular tethers 270 attached to the apical epicardial securing device.

Figure 11:
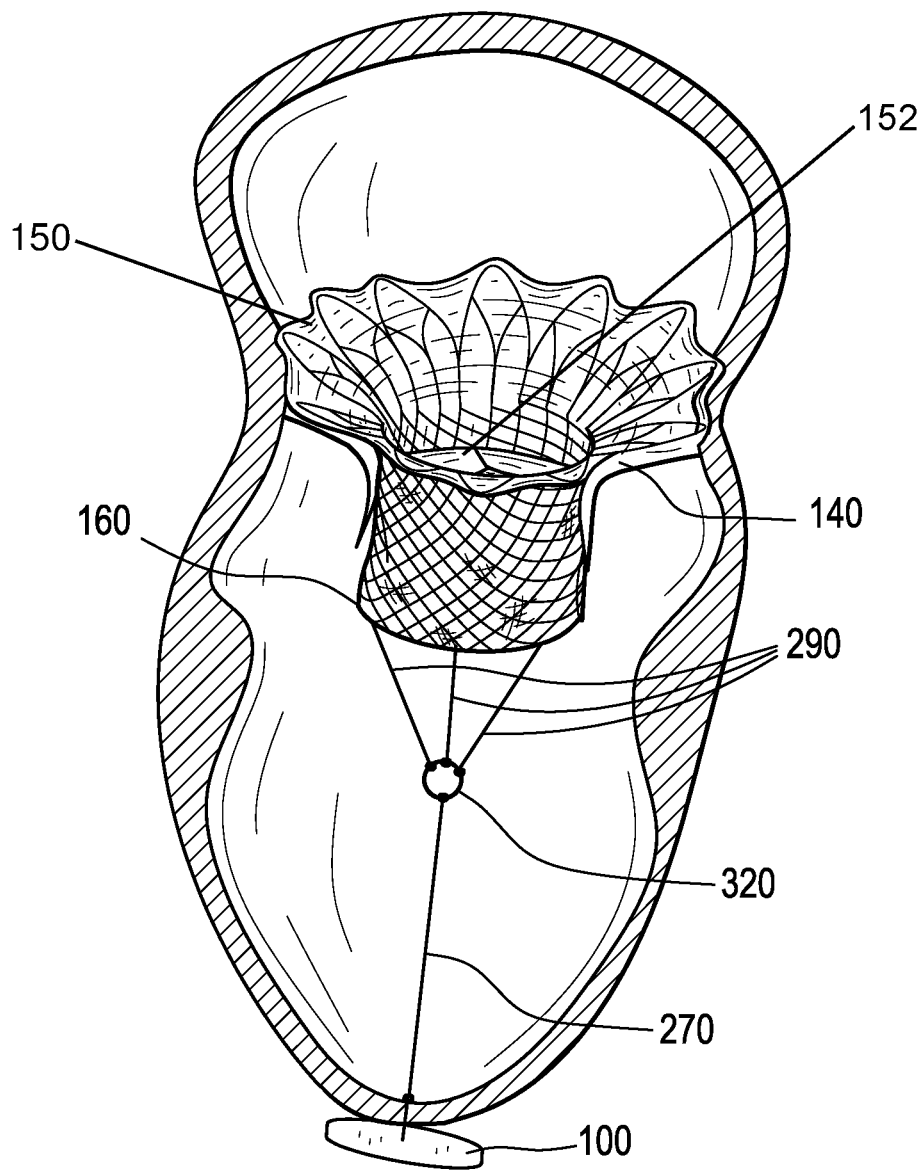
FIG. 11 is an illustration of a prosthetic mitral valve deployed within the mitral annulus with the upper cuff located in the left atrium and lower stent body in or towards the left ventricle.

FIG. 11 is an illustration of a prosthetic mitral valve deployed within the mitral annulus with the upper cuff 150 and leaflet assembly 152 located in the left atrium and lower stent body 160 in or towards the left ventricle. FIG. 11 shows a three (3) connection stent-tether system with three (3) centering tethers 290 connected to the stent body and converging to a polymeric intraventricular connecting ring 320. The ventricular tether 270 is in this embodiment is a single (1) tether and is connecting the connecting ring 320 to the apical epicardial tether securing device 100.

INCORPORATION AND EQUIVALENTS

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

What is claimed is:

1. A method, comprising:
deploying a prosthetic heart valve within a left atrium of a heart of a patient using a catheter inserted through an opening in an apex portion of the heart;
the prosthetic heart valve including (1) an expandable tubular stent body portion, a cuff and a leaflet assembly, (2) a plurality of tether members each having a first end permanently coupled directly to the expandable tubular stent body portion, and (3) a single anchoring tether having a first end coupled to a second end of the plurality of tether members, the single anchoring tether being separate from the plurality of tether members; and
securing a second end of the single anchoring tether to an epicardial surface location outside of the heart with a tether securing device, the tether securing device including at least one laterally extending pin hole configured to receive a pin, the securing including piercing the single anchoring tether with a first end of the pin so that an entirety of the pin is positioned within the pin hole, the pin having a second free end opposite the first end.

2. The method of claim 1, wherein the tether securing device defines a longitudinally extending interior region, the at least one laterally extending pin hole in fluid communication with the interior region, the method further comprising:
prior to securing the second end of the single anchoring tether, inserting the single anchoring tether through the longitudinally extending interior region.

3. The method of claim 1, wherein the plurality of tether members includes one of two tether members, three tether members and four tether members.

4. The method of claim 1, wherein the single anchoring tether is coupled to the plurality of tether members at a tether coupler.

5. The method of claim 4, wherein the tether coupler includes a tether loop, the second end of each tether member from the plurality of tether members being coupled to the tether loop, the first end of the single anchoring tether being coupled to the tether loop.

6. The method of claim 4, wherein the tether coupler includes a first tether loop and a second tether loop configured to be coupled to the first tether loop, the first tether loop configured to be moved between an open position and a closed position, the method further comprising:
prior to securing the second end of the single anchoring tether to the epicardial surface location outside the heart, coupling the second tether loop to the first tether loop when the first tether loop is in the open position, the second end of each tether member from the plurality of tether members being coupled to the first tether loop, the single anchoring tether being coupled to the second tether loop, the second tether loop configured to be coupled to the first tether loop when the first tether loop is in the open position, the first tether loop configured to be moved to the closed position to secure the second tether loop thereto.

7. The method of claim 1, wherein the first end of the plurality of tether members is fixedly coupled directly to the expandable tubular stent body portion.

8. The method of claim 1, further comprising:
during the deploying of the prosthetic valve, adjusting the single anchoring tether to a desired length associated with the anatomy of the patient.

9. The method of claim 1, further comprising:
during the deploying of the prosthetic valve, pulling the tethers such that the cuff is tightened onto tissue around the annulus of a native mitral valve to create a leak-free seal.

10. An apparatus, comprising:
a prosthetic heart valve including (1) an expandable tubular stent body portion, a cuff and a leaflet assembly, (2) a plurality of tethers having a first end coupled directly to the expandable tubular stent body portion, and (3) only a single anchoring tether having a first end and a second end, the first end of the single anchoring tether coupled to a second end of the plurality of tether members and the second end of the single anchoring tether configured to extend through the heart and be secured to an epicardial surface location outside of the heart when the prosthetic heart valve is implanted within the heart, the single anchoring tether being separate from the plurality of tether members, the plurality of tether members and the expandable tubular stent body portion being laser cut with pre-determined shapes to facilitate collapsing into a catheter delivery system;
a tether securing device including at least one laterally extending pin hole; and
a pin configured to pierce the single anchoring tether with a first end of the pin and to be received entirely within the pin hole to secure the second end of the single anchoring tether to the epicardial surface location outside of the heart, the pin having a second free end opposite the first end.

11. The apparatus of claim 10, wherein the tubular stent body portion and the plurality of tether members are formed from the same piece of superelastic or shape-memory metal.

12. The apparatus of claim 11, wherein the shape-memory metal is a nickel-titanium alloy.

13. The apparatus of claim 10, wherein the plurality of tether members includes one of two tether members, three tether members and four tether members.

14. The apparatus of claim 10, wherein each tether member from the plurality of tether members being coupled to a tether coupler proximal of the expandable tubular stent body, and the first end of the single anchoring tether being coupled to the tether coupler.

15. The apparatus of claim 14, wherein the tether coupler includes a tether loop, each tether member from the plurality of tether member being coupled to the tether loop, the first end of the single anchoring tether being coupled to the tether loop.

16. The apparatus of claim 14, wherein the tether coupler includes a first tether loop and a second tether loop configured to be coupled to the first tether loop, the first tether loop configured to be moved between an open position and a closed position, each tether member from the plurality of tether members being coupled to the first tether loop, the single anchoring tether being coupled to the second tether loop, the second tether loop configured to be coupled to the first tether loop when the first tether loop is in the open position, the first tether loop configured to be moved to the closed position to secure the second tether loop thereto.

17. The apparatus of claim 10, the tether securing device defining a longitudinally extending interior region, the at least one laterally extending pin hole intersecting the longitudinally extending interior region, the longitudinally extending interior region configured to receive the second end of the single anchoring tether therein.

* * * * *